United States Patent
Lee et al.

(10) Patent No.: US 8,075,583 B2
(45) Date of Patent: Dec. 13, 2011

(54) CATHETER WITH A POLYIMIDE DISTAL TIP

(75) Inventors: Jeong S. Lee, Diamond Bar, CA (US); Edwin Wang, Tustin, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1495 days.

(21) Appl. No.: 11/237,376

(22) Filed: Sep. 28, 2005

(65) Prior Publication Data
US 2006/0030874 A1 Feb. 9, 2006

Related U.S. Application Data

(62) Division of application No. 09/957,593, filed on Sep. 19, 2001, now Pat. No. 6,979,342.

(51) Int. Cl.
*A61M 29/00* (2006.01)
(52) U.S. Cl. .................................... 606/192; 604/96.01
(58) Field of Classification Search .................. 606/192, 606/194, 196, 198; 604/96.01, 97–99, 103, 604/104, 523, 524, 280; 623/1.11; 428/36.8
See application file for complete search history.

(56) References Cited

U.S. PATENT DOCUMENTS

| | | | |
|---|---|---|---|
| 4,636,346 A | 1/1987 | Gold et al. | |
| 4,659,622 A | 4/1987 | Barta et al. | |
| 4,826,706 A | 5/1989 | Hilker et al. | |
| 5,318,525 A | 6/1994 | West et al. | |
| 5,318,832 A | 6/1994 | Fishel et al. | |
| 5,454,788 A | 10/1995 | Walker et al. | |
| 5,470,315 A * | 11/1995 | Adams | 604/103.09 |
| 5,476,477 A | 12/1995 | Burns | |
| 5,496,275 A | 3/1996 | Sirhan et al. | |
| 5,499,973 A | 3/1996 | Saab | |
| 5,538,513 A * | 7/1996 | Okajima | 604/527 |
| 5,545,134 A * | 8/1996 | Hilaire et al. | 604/103.04 |
| 5,669,383 A | 9/1997 | Johnson | |
| 5,728,063 A | 3/1998 | Preissman et al. | |
| 5,759,173 A | 6/1998 | Preissman et al. | |
| 5,916,214 A | 6/1999 | Cosio et al. | |
| 6,010,521 A | 1/2000 | Lee et al. | |
| 6,171,275 B1 * | 1/2001 | Webster, Jr. | 604/20 |
| 6,217,565 B1 | 4/2001 | Cohen | |
| 6,245,053 B1 | 6/2001 | Benjamin | |
| 6,520,934 B1 | 2/2003 | Lee et al. | |
| 6,562,022 B2 * | 5/2003 | Hoste et al. | 604/524 |
| 6,620,127 B2 | 9/2003 | Lee et al. | |
| 6,663,614 B1 | 12/2003 | Carter | |
| 6,863,678 B2 | 3/2005 | Lee et al. | |
| 6,979,342 B2 * | 12/2005 | Lee et al. | 606/192 |

OTHER PUBLICATIONS

The Manufacturing Process section of the Phelps Dodge High Performance Conductors brochure, A Primer on Polyimide Tubing, pp. 1.

* cited by examiner

*Primary Examiner* — Victor Nguyen
(74) *Attorney, Agent, or Firm* — Fulwider Patton LLP; Thomas H. Majcher, Esq

(57) ABSTRACT

A catheter having an elongated shaft which has a multilayered distal tip with a first layer formed of a polyimide first material and a second layer formed of a polymeric second material. In one embodiment the multilayered distal tip is a separate member, distal to the distal end of a proximal portion of the shaft. In another embodiment, the shaft has an outer tubular member, and a multilayered inner tubular member with a distal end which forms the multilayered distal tip of the shaft. In a presently preferred embodiment, the polyimide material is a thermoset polyimide. In one embodiment, the polymeric second material is a polyamide material.

12 Claims, 2 Drawing Sheets

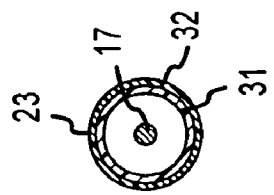
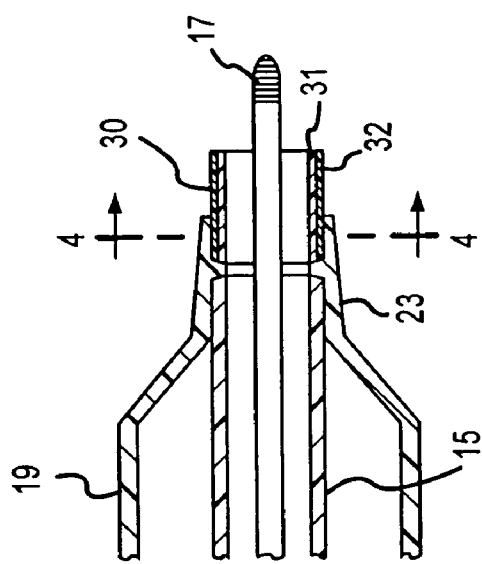
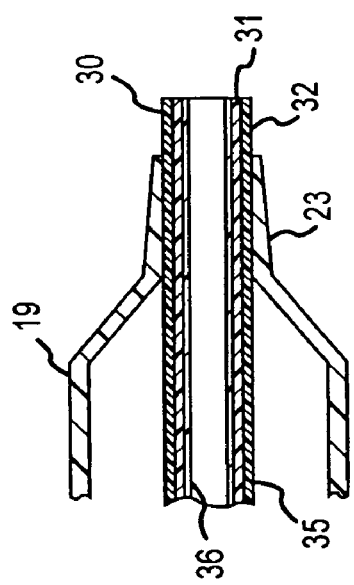
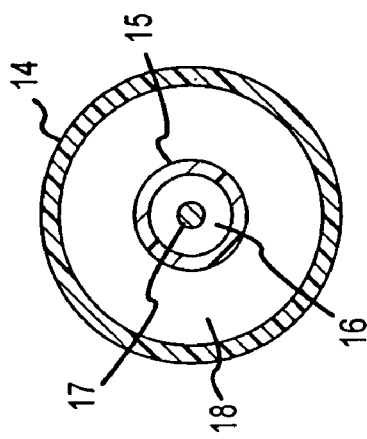

CATHETER WITH A POLYIMIDE DISTAL TIP

This application is a divisional of allowed U.S. patent application Ser. No. 09/957,593, filed Sep. 19, 2001 now U.S. Pat. No. 6,979,342.

BACKGROUND OF THE INVENTION

This invention generally relates to catheters, and particularly intravascular balloon catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy where the balloon of the dilatation catheter is positioned within the stenosis to be dilated. The balloon is then inflated with radiopaque liquid at relatively high pressures (generally 4-16 atmospheres) to dilate the stenosed region of the diseased artery. One or more inflations may be needed to effectively dilate the stenosis. Additionally, a stent may be implanted within the artery, typically by delivery to a desired location within the artery in a contracted condition on a balloon of a catheter which is similar in many respects to a balloon angioplasty catheter and expansion to a larger diameter by inflation of the balloon.

Prior art intravascular catheters have commonly included a soft distal tip to prevent or minimize injury to the vessel during advancement of the catheter therein. A balance is typically struck between stiffness and flexibility at the distal tip. Stiffness and strength provide improved ability to advance the catheter across an occlusion in the patient's vasculature, and can be a result of forming a secure connection between the tip and the section of the shaft proximal thereto shaft. On the other hand, flexibility at the distal end of the catheter results in improved maneuverability of the catheter and a more atraumatic distal end. Additionally, the soft tip preferably has a low profile for improved cross, yet a sufficiently large inner lumen to allow for guidewire movement therein.

Accordingly, it would be a significant advance to provide a catheter with a distal tip having improved performance. This invention satisfies these and other needs.

SUMMARY OF THE INVENTION

The invention is directed to a catheter having an elongated shaft which has a multilayered distal tip with a first layer formed of a polyimide first material and a second layer formed of a polymeric second material. In one embodiment the multilayered distal tip is a separate member, located distal to the distal end of a proximal portion of the shaft. In another embodiment, the shaft has an outer tubular member, and a multilayered inner tubular member with a distal end which forms the multilayered distal tip of the shaft.

In a presently preferred embodiment, the catheter is a balloon catheter generally comprising an elongated shaft having a proximal shaft section and a distal shaft section, with a balloon on the distal section of the shaft. The balloon catheters of the invention may comprise a variety of suitable balloon catheters, including coronary and peripheral dilatation catheters, stent delivery catheters, drug delivery catheters, and the like. The balloon catheter can be an over-the-wire catheter with a guidewire lumen extending the length of the shaft, or alternatively, a rapid exchange catheter with a short guidewire lumen in a distal shaft section.

In one embodiment, the polymeric second material is selected from the group consisting of a polyamide material and a polyurethane material. A variety of suitable polyamides can be used such as nylon, and copolyamides such as polyether block amide (PEBAX) available from Elf Autochem. A presently preferred polyurethane for the second layer is polyurethane N, available from Phelps Dodge High Performance Conductors. The polyimide first material is not compatible with the polyamide or polyurethane second material, and consequently, the polyimide material is not fusion (i.e., thermal) bondable thereto. The polyimide material is a high strength material preferably having a higher Shore durometer hardness than the second material. The high strength of the polyimide material allows the wall thickness of the polyimide first layer to be small for improved distal tip flexibility and low profile. Thus, despite the stiffness of the polyimide material, the distal tip has good flexibility due to the small wall thickness of the polyimide layer. The second layer provides a bonding layer which can be fusion bonded to polymeric materials such as polyamides and polyurethanes conventionally used for other catheter components such as balloons. In a presently preferred embodiment, the second layer is on an outer surface of the polyimide first layer. Preferably, the second layer is an outer layer forming an outer surface of the multilayered distal tip, for bonding to other components of the catheter. In one embodiment, the polyimide first layer forms an inner surface of the multilayered distal tip and thus defines the lumen of the distal tip. However, in the embodiment in which the distal tip is formed by the distal end of a multilayered inner tubular member, and not by a separate member distal thereto, the multilayered inner tubular member typically has a lubricious inner liner on an inner surface of at least a section of the polyimide layer, so that the lubricious liner forms the inner surface of at least a section of the inner tubular member. A variety of suitable materials can be used for the lubricious liner such as high density polyethylene (HDPE) and fluoropolymers such as polytetrafluoroethylene (PTFE). The lubricious inner liner is typically provided in the portion of the inner tubular member forming the distal tip. Alternatively, the lubricious inner liner has a distal end located proximally from the proximal and/or distal end of the distal tip. Similarly, a lubricious liner can be provided on an inner surface of the distal tip in the embodiment in which the distal tip is formed as a separate member distal to the inner member.

In a presently preferred embodiment, the polyimide material is a thermoset polyimide. However, in alternative embodiments, a thermoplastic polyimide is used. The thermoset polyimide has a very high glass transition temperature (Tg) of approximately 400° C. (as measured by differential scanning calorimetry), and excellent dimensional stability at the processing temperature of polyamides commonly used in catheter components. As a result, during formation and assembly of the catheter, production of a thin polyimide layer with controlled dimensions is facilitated.

In a presently preferred embodiment, the second layer is in direct contact with the polyimide first layer around a circumference thereof. Thus, unlike catheter shafts having a braid layer between a first and second layer, the first layer and the second layer of the multilayered distal tip are not in whole or in part separated from one another by a braid, mesh or other layer. Additionally, preferably, the polymeric second material of the second layer forms a solid-walled section of the second layer, so that the second layer is not itself a braid or mesh.

In a presently preferred embodiment, the polyimide first layer is formed by a solution process, and not by melt extrusion. In a suitable solution forming process, a polyimide solution is dip, or otherwise, coated onto a neckable mandrel, as described in U.S. Pat. Nos. 4,826,706 and 4,659,622, and the Manufacturing Process section of the Phelps Dodge High Performance Conductors brochure, A Primer on Polyimide Tubing, pp. 1, incorporated by reference herein in their entireties, and then separated intact from the mandrel, to thereby produce a tubular member. The dip coated mandrel can be passed through dies to control the outer dimension of the polyimide layer, and the diameter of the removable mandrel determines the inner diameter of the polyimide tube. Similarly, the second layer is preferably applied as a solution onto the polyimide layer, in order to provide good contact and adhesion between the polyimide layer and the second layer. Thus, although the polyimide material is not fusion bondable to the polymeric second material (e.g., polyamide or polyurethane material), the solution coating process provides well adhered layers which remain together during component assembly and under the high inflation pressures used during inflation of the catheter balloon. As a result, a separate adhesive or compatibilizing layer is not required between the polyimide layer and the second layer, and, consequently, the multilayered distal tip of the invention has excellent flexibility, manufacturability, and low profile.

The distal tip of the invention has improved flexibility and low profile, due at least in part to the thinness of the polyimide layer. Additionally, the distal tip facilitates use of the catheter to cross a tight or chronic total occlusion (CTO), due to the low profile and strong distal tip provided by the high modulus polyimide layer. In one embodiment, the distal tip thermoset polyimide has excellent dimensional stability during assembly of the catheter, providing a distal tip with improved controlled, low profile dimensions. In the embodiment in which the polyimide layer and the second polymer layer are formed by a dip coating process, the distal tip has improved flexibility despite the layers not being fusion bondable together, due to the lack of an adhesive or compatibilizing layer otherwise required for securing noncompatible layers together.

BRIEF DESCRIPTION OF THE DRAWINGS

FIG. 2 illustrates an enlarged, partially in section, view of the distal end of the catheter shown in FIG. 1, taken within circle 2.

FIG. 3 is a transverse cross sectional view of the catheter shown in FIG. 1, taken along line 3-3.

FIG. 4 is a transverse cross sectional view of the catheter shown in FIG. 2, taken along line 4-4.

FIG. 5 illustrates an enlarged longitudinal cross section of an alternative embodiment of a distal tip which embodies features of the invention, in which the distal end of a multilayered inner tubular member forms the multilayered distal tip.

DETAILED DESCRIPTION OF THE INVENTION

Figure 1:
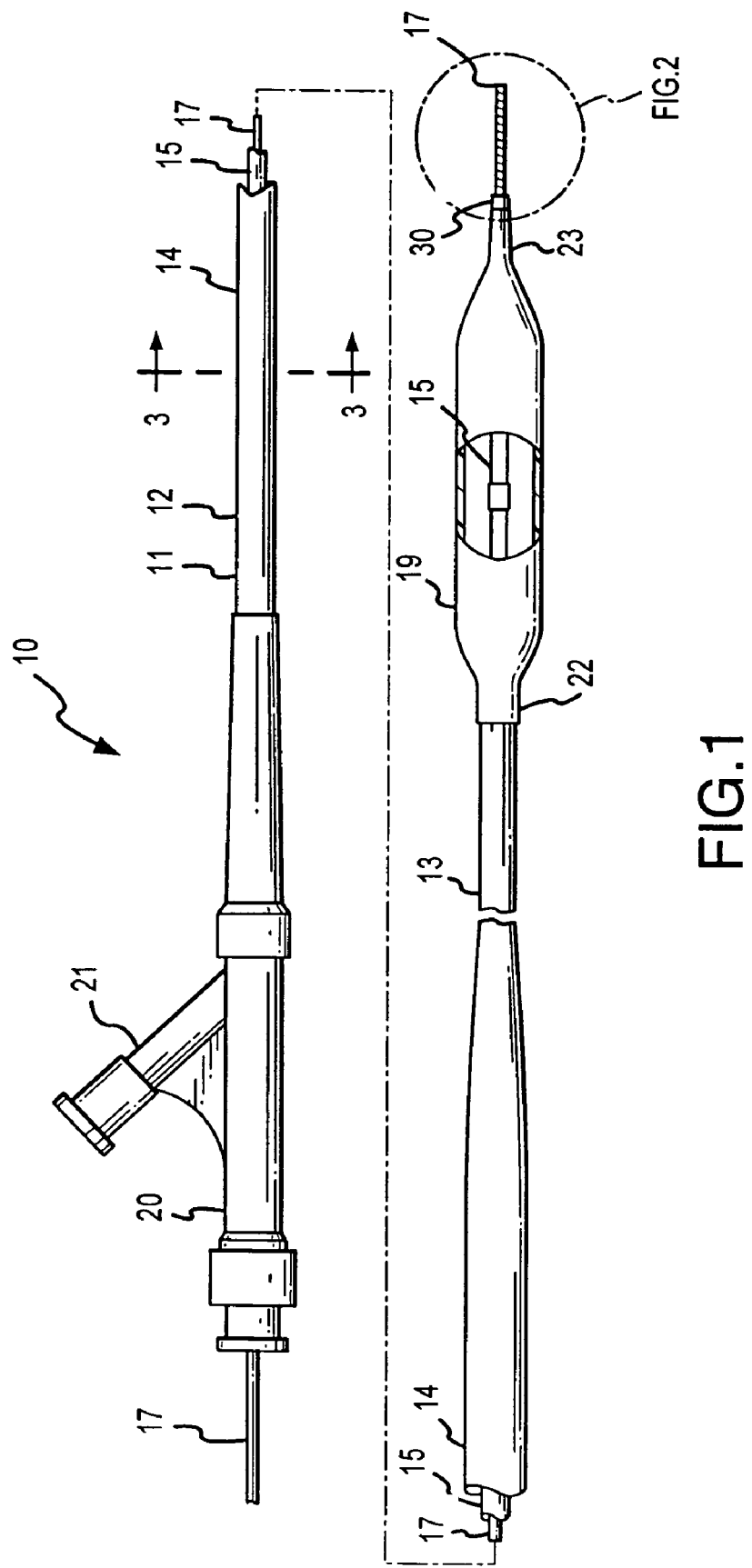
FIG. 1 is an elevational view, partially in section, of a catheter which embodies features of the invention.

FIGS. 1-4 illustrate an over-the-wire type balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17, and the coaxial relationship between outer tubular member 14 and inner tubular member 15 defines annular inflation lumen 18 (see FIG. 3, illustrating a transverse cross section of the catheter 10 of FIG. 1, taken along line 3-3). An inflatable balloon 19 is disposed on the distal shaft section 13, having a proximal skirt section sealingly secured to the distal end of outer tubular member 14, and a distal skirt section sealingly secured to the distal end of inner tubular member 15, so that its interior is in fluid communication with inflation lumen 18. An adapter 20 at the proximal end of the shaft is configured to provide access to guidewire lumen 17, and to direct inflation fluid through arm 21 into inflation lumen 18. Balloon 19 has an inflatable working length located between tapered sections of the balloon. FIG. 1 illustrates the balloon 19 in an uninflated configuration prior to inflation. The distal end of catheter may be advanced to a desired region of a patient's body lumen in a conventional manner, and balloon 19 inflated to perform a procedure such as dilatation of a stenosis.

The catheter shaft has a distal tip 30 at the distal end of the catheter. As best illustrated in FIG. 2, showing an enlarged longitudinal cross sectional view of the catheter 10 shown in FIG. 1, taken within circle 2, the distal tip 30 is multilayered with a first layer 31 of a polyimide material and a second layer 32 of a material which is different from the first material, and which is preferably a polyamide material or a polyurethane material. A presently preferred polyamide for the second layer is PEBAX, available from Elf Autochem. A presently preferred polyimide for the first layer is available from Phelps Dodge High Performance Conductors. Preferably, the polyimide is a thermoset polyimide with excellent dimensional stability, which thus has a cross linked 3-dimensional network maintained a high temperatures. The second layer 32 is on an outer surface of the first layer 31. As illustrated in the figures, the second layer 32 is a solid-walled layer, which is in direct contact with the first layer 31 around a circumference of the first layer 31. Thus, the second layer 32 is not separated from the first layer 31 by an intermediate layer or braid, and is not itself a braid or mesh.

In the embodiment of FIG. 2, the second layer 32 is an outer layer forming an outer surface of the distal tip 30. Thus, although a coating such as a lubricious coating conventionally used on catheter shafts may optionally be provided on at least a section of the multilayered distal tip 30, a structural or reinforcing layer is not on an outer surface of the second layer 32, in the embodiment of FIG. 2. The balloon distal shaft section 23 is bonded, and preferably fusion bonded, to the second layer 32 of the distal tip 30. Thus, the balloon 19 is preferably formed of a polymeric material which is compatible and therefore fusion bondable to the polymeric material of the second layer 32. As a result, adhesive or compatibilizing materials are not required at the distal tip, and the catheter distal end has high flexibility. In one embodiment, the balloon 19 is formed of a polyamide or a polyurethane. The balloon 19 may be a single layered balloon, or a multilayered balloon with at least one layer formed of the polyamide or polyurethane material bonded to the second layer of the distal tip 30.

In the embodiment illustrated in FIG. 2, the distal tip 30 is formed of a separate member indirectly bonded to the distal end of the inner tubular member. The distal skirt section 23 of the balloon 19 is bonded to a proximal portion of the distal tip member 30 and to a distal portion of the inner tubular member 15. The distal skirt section 23 of the balloon 19 thus indirectly secures the distal tip member 30 to the inner tubular member 15, due to the gap between the proximal end of the distal tip member 30 and a distal end of the inner tubular member 15. The gap can be filled in whole or in part by balloon material. In the embodiment illustrated in FIG. 2, the first layer 31 forms an inner surface of the multilayered section of the outer tubular member 32. Although not illustrated, a lubricious liner may be provided on the inner surface of distal tip 30 and/or the inner tubular member 15 of the embodiment of FIG. 2. However, for ease of manufacturing, a lubricious liner is typically not provided on the inner surface of distal tip 30.

FIG. 5 illustrates an alternative embodiment of the distal tip of the invention in which the multilayered distal tip 30 is formed by the distal end of a multilayered inner member 35 having polyimide first layer 31 and second layer 32. In the embodiment illustrated in FIG. 5, a liner 36 formed of a lubricious material, such as PTFE or HDPE, different from the polyimide material is on an inner surface of the inner tubular member 35 to facilitate guidewire movement therein as is conventionally known.

When the catheter of the invention is used in an angioplasty procedure, the balloon catheter of the invention is advanced over the guidewire until the balloon is properly positioned across the stenosis. The balloon 19 can be inflated in a conventional manner by introducing inflation fluid through the inflation lumen into the balloon 19. After one or more inflations, the balloon is deflated and the catheter removed from the patient. A similar procedure is used when the balloon has a stent (not shown) mounted thereon for implanting in the body lumen.

The length of the dilatation catheter is generally about 137 to about 145 centimeters, and typically about 140 centimeters for PTCA. The outer tubular member 14 distal section has an outer diameter (OD) of about 0.028 to about 0.036 inch (0.70-0.91 mm), and an inner diameter (ID) of about 0.024 to about 0.035 inch (0.60-0.89 mm), and the outer tubular member 14 proximal section has an OD of about 0.017 to about 0.034 inch (0.43-0.87 mm), and an inner diameter (ID) of about 0.012 to about 0.022 inch (0.30-0.56 mm). The inner tubular member 15 has an OD of about 0.017 to about 0.026 inch (0.43-0.66 mm), and an ID of about 0.015 to about 0.018 inch (0.38-0.46 mm) depending on the diameter of the guidewire to be used with the catheter. The distal tip 30 has an OD of about 0.017 in (0.43 mm) and an ID of about 0.0158 inch (0.4 mm). The wall thickness of the distal tip 30 is preferably about 0.001 inches (0.025 mm) or less. In one embodiment, the polyimide first layer 31 has a wall thickness of about 0.001 inch (0.025 mm) to about 0.0015 inch (0.038 mm), and the second layer 32 has a wall thickness of about 0.0003 inches (0.0076 mm) to about 0.0005 inches (0.0127 mm). In a presently preferred embodiment, the polyimide first layer 31 of the distal tip 30 has a greater thickness than the second layer 32.

While the present invention has been described herein in terms of certain preferred embodiments, those skilled in the art will recognize that modifications and improvements may be made without departing form the scope of the invention. For example, while the catheter illustrated in the figures is an over-the-wire catheter with an inner tubular member coaxial with the outer tubular member and extending from the proximal end of the shaft, other conventional catheter shaft configurations can be used, such as rapid exchange type catheter designs, and other configurations can be used along at least a section of the catheter, such as side-by-side, dual lumen configurations. In a rapid exchange catheter, the catheter generally includes a distal guidewire port on a distal end of the catheter, and a proximal guidewire port distal to the proximal end of the shaft and typically spaced a relatively short distance from the distal end of the shaft and a relatively long distance from the proximal end of the shaft, and a guidewire lumen extending therebetween. Additionally, although not illustrated, the balloon catheter can be used to deliver and implant a stent within the patient's body lumen. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A catheter, comprising an elongated shaft having a proximal shaft section, a distal shaft section, and a multilayered distal tip at a distal end of the catheter with a lumen, the distal tip having a first layer formed of a polyimide first material and a second layer formed of a polymeric second material not fusion bondable to the polyimide first material, wherein said first and second layer are adhered to one another but no adhesive is present between said first and second layers, wherein the second layer of the distal tip is in direct contact with the first layer around a circumference of the first layer.

2. The catheter of claim 1 wherein the polymeric second material is selected from the group consisting of polyamide, nylon, polyether block amide, and polyurethane.

3. The catheter of claim 1 wherein the polymeric second material has a lower Shore durometer hardness than the polyimide first material.

4. The catheter of claim 1 wherein the second layer is an outer layer forming an outer surface of the distal tip.

5. The catheter of claim 1 wherein the polyimide first material is a thermoset polyimide.

6. The catheter of claim 1 wherein the polyimide first layer is an inner layer forming an inner surface of the distal tip, defining the lumen of the distal tip.

7. The catheter of claim 1 wherein the second layer is solid-walled.

8. The catheter of claim 1 wherein the catheter is a balloon catheter with a balloon having a distal skirt section bonded to the second layer of the distal tip.

9. The catheter of claim 1 wherein the polyimide first layer is on an inner surface of the second layer.

10. The catheter of claim 1 including a lubricious liner on the inner surface of the polyimide first layer, which defines the lumen of the distal tip.

11. The catheter of claim 1 wherein the distal shaft section has a proximal tubular member with at least one lumen in fluid communication with the distal tip lumen, and the distal tip is a distal tip member located distal to the proximal tubular member.

12. The catheter of claim 11 wherein the distal tip member has a proximal end bonded to a distal end of the proximal tubular member.

* * * * *